United States Patent

Fetzer et al.

[11] Patent Number: 6,133,482
[45] Date of Patent: Oct. 17, 2000

[54] METHOD FOR PRODUCING CARBONYL COMPOUNDS

[75] Inventors: Thomas Fetzer, Speyer; Dirk Demuth, Mannheim; Heinz Rütter, Hochdorf-Assenheim; Helmuth Menig, Friedelsheim; Peter Resch, Hettenleidelheim; Wilhelm Ruppel, Frankenthal; Harro Wache, Fussgönheim, all of Germany

[73] Assignee: BASF Aktiengesellschaft, Ludwigshafen, Germany

[ * ] Notice: This patent is subject to a terminal disclaimer.

[21] Appl. No.: 09/331,063
[22] PCT Filed: Dec. 23, 1997
[86] PCT No.: PCT/EP97/06856
 § 371 Date: Jun. 16, 1999
 § 102(e) Date: Jun. 16, 1999
[87] PCT Pub. No.: WO98/28251
 PCT Pub. Date: Jul. 2, 1998

[30] Foreign Application Priority Data

Dec. 23, 1996 [DE] Germany .......................... 196 54 054

[51] Int. Cl.$^7$ .................................................. C07C 45/29
[52] U.S. Cl. .......................... 568/473; 568/471; 568/472
[58] Field of Search ..................................... 568/338, 344, 568/347, 357, 361, 383, 399, 402, 469, 471, 472, 473, 489, 494, 852

[56] References Cited

U.S. PATENT DOCUMENTS

| | | | |
|---|---|---|---|
| 4,282,374 | 8/1981 | Engelbach et al. | 568/471 |
| 4,503,261 | 3/1985 | Sauer et al. | 568/471 |
| 4,555,583 | 11/1985 | Toyoda et al. | 568/473 |
| 4,814,513 | 3/1989 | Graf et al. | 568/471 |

FOREIGN PATENT DOCUMENTS

| | | |
|---|---|---|
| 007 570 | 2/1980 | European Pat. Off. . |
| 271 812 | 6/1988 | European Pat. Off. . |

*Primary Examiner*—Sreeni Padmanabhan
*Attorney, Agent, or Firm*—Keil & Weinkauf

[57] ABSTRACT

In a process for preparing carbonyl compounds of the formula

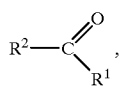

I where $R^1$ is a hydrogen atom or an alkyl radical having from 1 to 3 carbon atoms, $R^2$ is a hydrogen atom or a radical of the formula

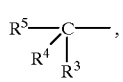

II where $R^3$ is a hydrogen atom or together with $R^4$ is an oxygen atom, $R^4$ is the radical $OR^6$ or together with $R^3$ is an oxygen atom, $R^5$ is a hydrogen atom, an alkyl radical having from 1 to 8 carbon atoms or a cyclohexyl or cyclopentyl radical and $R^6$ is an alkyl radical having from 1 to 4 carbon atoms, a cyclohexyl or cyclopentyl radical or a radical of the formula —CH$_2$—CHO or —CH$_2$—CH$_2$—O—CH$_2$—CHO, by gas-phase oxidation of methanol or alcohols of the formula

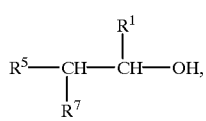

III where $R^1$ and $R^5$ are as defined above and $R^7$ is a hydrogen atom or a radical $OR^8$ and $R^8$ is a hydrogen atom, an alkyl radical having from 1 to 4 carbon atoms, a cyclohexyl or cyclopentyl radical or a radical for the formula —CH$_2$—CH$_2$—OH or —CH$_2$—CH$_2$—O—CH$_2$—CH$_2$—OH, using an oxygen-containing gas in the presence of copper- and/or silver-containing catalysts and an amount of a phosphorus compound which is volatile under the reaction conditions which is such that the amount of phosphorus (calculated as P) is up to 20 ppm, based on the weight of alcohol used, the phosphorus is introduced within the catalyst bed.

7 Claims, No Drawings

METHOD FOR PRODUCING CARBONYL COMPOUNDS

The U.S. National Stage Application of PCT/EP97/06856 filed Dec. 23, 1997.

FIELD OF THE INVENTION

The present invention relates to a novel process for preparing carbonyl compounds by gas-phase oxidation of alcohols using an oxygen-containing gas in the presence of copper- and/or silver-containing catalysts and a phosphorus compound which is volatile under the reaction conditions and is introduced directly into the catalyst bed.

BACKGROUND OF THE INVENTION

Processes for preparing carbonyl compounds by gas-phase oxidation over copper or silver catalysts in the presence of volatile phosphorus compounds are known from the prior art.

Thus, EP-A 007 570 describes a process for preparing glyoxal by gas-phase oxidation of ethylene glycol by oxygen over a copper-containing oxidation catalyst in the presence of phosphorus compounds which are volatile under the reaction conditions, in which the amount of phosphorus of from 1 to 100 ppm, based on ethylene glycol used, is added with the starting compounds. These processes give unsatisfactory glyoxal yields of up to 70 mol %, based on ethylene glycol reacted.

According to the processes of U.S. Pat. No. 4,282,374 and U.S. Pat. No. 4,503,261, advantageous results in respect of the life of the catalysts and the glyoxal yield are obtained in the gas-phase oxidation of ethylene glycol over copper catalysts or over a layer catalyst of copper and silver crystals if the reaction is carried out in the presence of a volatile phosphorus compound, with the amount of phosphorus (calculated as P) being from 1 to 100 ppm or from 0.5 to 20 ppm, based on the weight of ethylene glycol, and the phosphorus being introduced together with the starting compounds upstream of the catalyst bed. However, in these processes it has been found that the glyoxal yield and product purity become increasingly worse with time on prolonged operation. This disadvantage is attributable to increased formation of formaldehyde and of $CO/CO_2$.

EP-B 0 271 812 proposes, for the preparation of carbonyl compounds such as glyoxal, a gas-phase oxidation of alcohols using an oxygen-containing gas in the presence of copper- or silver-containing catalysts and a phosphorus compound which is volatile under the reaction conditions, in which the phosphorus compound is mixed in one portion of less than 0.5 ppm, based on the weight of alcohol used and calculated as phosphorus, into the gaseous starting mixture prior to the reaction over the catalyst.

According to the process described in EP-B 0 271 812, glyoxal is obtained in yields of up to 80 mol %.

The above processes of the prior art have the disadvantage of an unsatisfactory yield. In the known processes, glyoxal is obtained as an aqueous solution contaminated with glycol aldehyde, formaldehyde and organic acids. Further undesired by-products are the combustion products CO, $CO_2$ and $H_2O$ which are formed. As a result of the by-products, the known processes have the additional disadvantage of unsatisfactory catalyst operating lives.

In addition, for many applications the presence of formaldehyde in the glyoxal is highly undesirable because of the toxicological properties and the high reactivity of the formaldehyde. Since formaldehyde can be removed from the crude glyoxal only at considerable expense and with the acceptance of yield losses, for example by treatment with steam or by chemical reaction, it would be useful to have a process which allows glyoxal to be prepared by catalytic gas-phase oxidation of ethylene glycol even at long operating times while largely avoiding the formation of interfering by-products.

DETAILED DESCRIPTION OF THE INVENTION

It is an object of the present invention to provide a process which meets these criteria.

We have found that this object is achieved in the preparation of carbonyl compounds of the formula

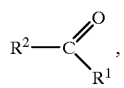

I where $R^1$ is a hydrogen atom or an alkyl radical having from 1 to 3 carbon atoms, $R^2$ is a hydrogen atom or a radical of the formula

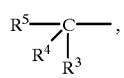

II where $R^3$ is a hydrogen atom or together with $R^4$ is an oxygen atom, $R^4$ is the radical $OR^6$ or together with $R^3$ is an oxygen atom, $R^5$ is a hydrogen atom, an alkyl radical having from 1 to 8 carbon atoms or a cyclohexyl or cyclopentyl radical and $R^6$ is an alkyl radical having from 1 to 4 carbon atoms, a cyclohexyl or cyclopentyl radical or a radical of the formula $—CH_2—CHO$ or $—CH_2—CH_2—O—CH_2—CHO$, by gas-phase oxidation of methanol or alcohols of the formula

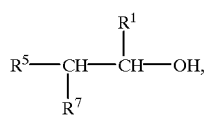

III where $R^1$ and $R^5$ are as defined above and $R^7$ is a hydrogen atom or a radical $OR^8$ and $R^8$ is a hydrogen atom, an alkyl radical having from 1 to 4 carbon atoms, a cyclohexyl or cyclopentyl radical or a radical of the formula $—CH_2—CH_2—OH$ or $—CH_2—CH_2—O—CH_2—CH_2—OH$, using an oxygen-containing gas in the presence of copper- and/or silver-containing catalysts and an amount of a phosphorus compound which is volatile under the reaction conditions which is such that the amount of phosphorus (calculated as P) is up to 20 ppm, preferably from 0.05 to 20 ppm, based on the weight of alcohol used, if the phosphorus is introduced within the catalyst bed, preferably in the region of the upper 0.1–50% of the total height of the catalyst bed, particularly preferably in the region of the upper 1–35% of the total height of the bed.

In the novel process, glyoxal is obtained from ethylene glycol in long-term operation in high yield and purity and with a significantly reduced formaldehyde content.

In the alcohols of the formula III, alkyl radicals are, for example, methyl, ethyl, propyl or butyl radicals. In the process of the present invention, the terminal hydroxyl groups are converted into aldehyde groups and the secondary hydroxyl groups into keto groups.

Examples of starting compounds of the formula III are:

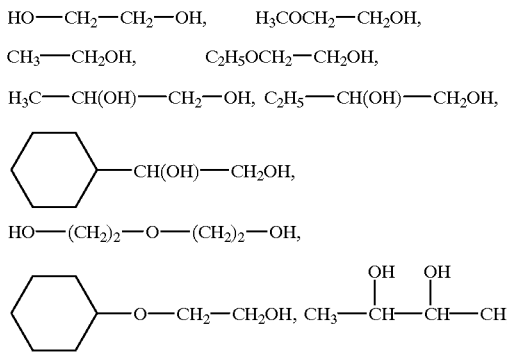

The gas-phase oxidation of the alcohol with the oxygen-containing gas over the copper- and/or silver-containing catalysts is carried out in a manner known per se, eg. at from 225 to 500° C. Examples of suitable copper- and/or silver-containing catalysts are metallic copper or silver, copper-containing or silver-containing alloys or compounds with metals or nonmetals, eg. copper phosphides, copper bronzes or alloys of copper with silver and/or gold, copper ores such as malachite and copper or silver compounds which can be completely or partially reduced to copper or silver during the reaction, eg. copper(I) oxide, silver(I) oxide, copper(II) oxide and compounds which are converted into copper oxides on heating, eg. copper nitrate and copper acetate. Further suitable compounds are copper phosphate and copper antimonate. Other metal or nonmetal oxides such as the oxides of zinc, chromium, phosphorus, antimony, tin and bismuth can additionally be mixed into the copper-containing compounds. The copper- and/or silver-containing catalytic composition can also be applied to an inert support or, if desired, diluted with an inert material. If desired, the catalyst can also be subjected to a reducing treatment before use.

Preference is given to catalysts which do not have a large internal surface area, for example those having a surface area of less than 50 m² per g. Of particular industrial interest are metallic copper or silver and alloys containing copper or silver as a significant constituent. They are employed, for example, in the form of turnings, wire meshes, gases or else as supported catalysts having a, for example, low surface area, inert support.

As phosphorus compounds which are volatile under the reaction conditions, use is advantageously made of phosphorus compounds which can be vaporized without decomposition and which do not undergo any reaction with the components of the synthesis gas under the reaction conditions. Such compounds are, for example, esters of phosphoric acid, of phosphorous acid or of phosphonic acid, eg. trimethyl phosphate, triethyl phosphate, triisopropyl phosphate, tri-n-propyl phosphate, trimethyl phosphite, triethyl phosphite, triethylphosphine oxide, diethyl methylphosphonate, dimethyl methylphosphonate or diethyl ethylphosphonate.

According to the process of the present invention, the phosphorus is introduced within the catalyst bed, preferably in the region of the upper 0.1–50% of the total height of the catalyst bed, particularly preferably in the region of the upper 1–35% of the catalyst bed, toward the top of the reactor. The introduction within the catalyst bed is preferably carried out downstream of the hot spot. For the purposes of the present invention, the hot spot is the part of the catalyst bed in which the highest temperature within the temperature profile of the catalyst bed occurs. The temperature profile of the catalyst bed or the position of the hot spot is customarily determined by determining the temperature within the catalyst bed as a function of the height within the bed. This can be achieved, for example, by insertion of a thermocouple tube having a movable thermocouple or else by means of a fixed multiple thermocouple having a plurality of measurement points at different heights within the bed.

The phosphorus can be introduced in a plurality of portions, for example two, three or four portions, with the addition preferably being carried out in two portions of from 0.05 to 10 ppm each, particularly preferably from 1 to 3 ppm each.

In the case of more than two points of addition, for example three points of addition, the total amount of the volatile phosphorus compound of 20 ppm is preferably divided up into portions of from 0.05 to 10 ppm.

The weight ratio of the first portion of the phosphorus to the second portion or the sum of the further portions is from 0.005 to 200, preferably from 0.033 to 30 and particularly preferably from 0.3 to 3.3.

The process of the present invention is, for example, carried out by passing a gaseous mixture of the alcohol and water, with the water content being from 0.1 to 99% by weight, together with air or oxygen in an amount of from 0.5 to 2.0 mol, based on 1 mol of alcohol used, possibly together with nitrogen in an amount of up to 99% by volume of the total gas mixture, over the catalyst held at from 225 to 500° C., with the volatile phosphorus compound being introduced into the catalyst bed downstream of the hot spot in the region of 1–35% of the total height of the bed.

The gas mixture leaving the reactor is usually scrubbed with water.

The phosphorus compound can be introduced as a solution in water, alcohol, preferably the alcohol used, or suitable solvents, such as ethers, in liquid form or, by vaporization of the solution, in gaseous form or else in the form of the pure gaseous phosphorus compound, with introduction as a vaporized solution or in pure gaseous form being preferred.

The glyoxal obtained from ethylene glycol by the process of the present invention can be obtained directly in the commercial form of a 40% strength by weight aqueous solution and has a high purity which remains unchanged even during a long operating time.

The process of the present invention gives glyoxal in high yields with long catalyst operating lives.

The process of the present invention is illustrated by the following examples.

EXPERIMENTAL DATA

EXAMPLE 1

7.2 kg of shaped copper bodies were installed in a tube reactor of stainless steel having an internal diameter of 55 mm to give a catalyst bed height of 250 cm (catalyst volume: 5.7 l). A synthesis gas mixture comprising 840 g of ethylene glycol, 1720 standard l of air and 230 standard l of nitrogen was passed per our through the tube reactor. At 24% of the total height of the catalyst bed downstream of the hot spot which was located at 15% of the total height of the bed, 0.3 ppm of P, based on the weight of ethylene glycol used, in the form of triethyl phosphate was added to the synthesis gas. The reactor temperature was set to 365° C. by means of a salt melt.

The total amount of gas, consisting of circulated gas and synthesis gas, was 9150 standard 1/h. The GHSV (gas hourly space velocity), which is defined as GHSV=Gas volume / catalyst volume, was 1610 h$^{-1}$. The LHSV (liquid hourly space velocity), which is defined as LHSV=Liquid volume / catalyst volume, was 0.13 h$^{-1}$. The residence time, defined as the quotient of the catalyst volume and the amount of gas, was 2.3 s.

After leaving the reactor, the reaction gas was contacted with water and the reaction products were dissolved in the aqueous phase. The permanent gases CO and $CO_2$ formed in the reaction remain3ed in the off-gas and were analyzed in the gas phase.

After a running time of 10 days, a glyoxal yield of 76.9 mol %, based on ethylene glycol used, was achieved at an ethylene glycol conversion of 98.0 mol %. Combustion to give CO and $CO_2$ was 12.9 mol %. Further by-products formed were 1.7 mol % of glycol aldehyde and 4.9 mol % of formaldehyde.

Comparative Example 1 (no addition of volatile P compound)

The procedure of Example 1 was repeated, but no volatile phosphorus compound was added. The product work-up and the analysis of the gas were carried out as described in Example 1. A glyoxal yield of 71.6 mol % was obtained at an ethylene glycol conversion of 94.3 mol %. Combustion to give CO and $CO_2$ was 13 mol %. Glycol aldehyde and formaldehyde were formed in amounts of 1.3 mol % and 6.1 mol % respectively.

Comparative Example 2 (addition of volatile P compounds to the feed mixture)

The procedure of Example 1 was repeated, but the triethyl phosphate was added upstream of the catalyst bed. 0.3 ppm of P, based on the weight of ethylene glycol used, in the form of triethyl phosphate was added to the synthesis gas upstream of the catalyst bed. The product work-up and the analysis of the gas were carried out as described in Example 1. A glyoxal yield of 75.9 mol % was obtained at an ethylene glycol conversion of 98.8 mol %. Combustion to give CO and $CO_2$ was 13.8 mol %. Glycol aldehyde and formaldehyde were formed in amounts of 1.1 mol % and 5.9 mol % respectively.

In Table 1 below, the conversions and yields achieved in Example 1 are compared with those in the Comparative Examples C1 and C2 which are not according to the present invention.

TABLE 1

| Example | Ethylene glycol conversion [mol %] | Glyoxal yield [mol %] | $CO/CO_2$ formation [mol %] | Glycol aldehyde formation [mol %] | Formaldehyde formation [mol %] |
| --- | --- | --- | --- | --- | --- |
| 1 | 98.0 | 76.9 | 12.9 | 1.6 | 4.9 |
| C1 | 94.3 | 71.6 | 13 | 1.3 | 6.1 |
| C2 | 98.8 | 75.9 | 13.8 | 1.1 | 5.9 |

EXAMPLE 2

7.2 kg of shaped copper bodies were installed in a tube reactor of stainless steel having an internal diameter of 55 mm to give a catalyst bed height of 250 cm (catalyst volume: 5.7 1). A synthesis gas mixture comprising 840 g of ethylene glycol, 1800 standard 1 of air and 150 standard 1 of nitrogen was passed per hour through the tube reactor. At 24% of the total height of the catalyst bed downstream of the hot spot which was located at 15% of the total height of the bed, 0.3 ppm of P, based on the weight of ethylene glycol used, in the form of triethyl phosphate was added to the synthesis gas. The reactor temperature was set to 365° C. by means of a salt melt.

The total amount of gas, consisting of circulated gas and synthesis gas, was 9150 standard 1/h. The GHSV (gas hourly space velocity), which is defined as GHSV=Gas volume / catalyst volume, was 1610 h$^{-1}$. The LHSV (liquid hourly space velocity), which is defined as LHSV=Liquid volume / catalyst volume, was 0.13 h$^{-1}$. The residence time, defined as the quotient of the catalyst volume and the amount of gas, was 2.3 s.

After leaving the reactor, the reaction gas was contacted with water and the reaction products were dissolved in the aqueous phase. The permanent gases CO and $CO_2$ formed in the reaction remained in the off-gas and were analyzed in the gas phase.

After a running time of 10 days, a glyoxal yield of 76.0 mol %, based on ethylene glycol used, was achieved at an ethylene glycol conversion of 98.7 mol %. Combustion to give CO and $CO_2$ was 14.4 mol %. Further by-products formed were 1.1 mol % of glycol aldehyde and 4.7 mol % of formaldehyde.

Comparative Example 3 (no addition of volatile P compound)

The procedure of Example 2 was repeated, but no volatile phosphorus compound was added. The product work-up and the analysis of the gas were carried out as described in Example 2. A glyoxal yield of 73.8 mol % was obtained at an ethylene glycol conversion of 98.2 mol %. Combustion to give CO and $CO_2$ was 14.9 mol %. Glycol aldehyde and formaldehyde were formed in amounts of 0.8 mol % and 5.8 mol % respectively.

Comparative Example 4 (addition of volatile P compounds to the feed mixture)

The procedure of Example 2 was repeated, but the triethyl phosphate was added upstream of the catalyst bed. 0.3 ppm of P. based on the weight of ethylene glycol used, in the form of triethyl phosphate was added to the synthesis gas upstream of the catalyst bed. The product work-up and the analysis of the gas were carried out as described in Example 2. A glyoxal yield of 74.5 mol % was obtained at an ethylene glycol conversion of 99.6 mol %. Combustion to give CO and $CO_2$ was 16 mol %. Glycol aldehyde and formaldehyde were formed in amounts of 0.5 mol % and 3.3 mol % respectively.

In Table 2 below, the conversions and yields achieved in Example 2 are compared with those in the Comparative Examples C3 and C4 which are not according to the present invention.

TABLE 2

| Example | Ethylene glycol conversion [mol %] | Glyoxal yield [mol %] | CO/CO$_2$ formation [mol %] | Glycol aldehyde formation [mol %] | Formaldehyde formation [mol %] |
| --- | --- | --- | --- | --- | --- |
| 2 | 98.7 | 76.0 | 14.4 | 1.1 | 4.7 |
| C3 | 98.2 | 73.8 | 14.9 | 0.8 | 5.8 |
| C4 | 99.6 | 74.5 | 16 | 0.5 | 3.3 |

EXAMPLE 3

7.2 kg of shaped copper bodies were installed in a tube reactor of stainless steel having an internal diameter of 55 mm to give a catalyst bed height of 250 cm (catalyst volume: 5.7 l). A synthesis gas mixture comprising 840 g of ethylene glycol, 1720 standard l of air and 230 standard l of nitrogen was passed per hour through the tube reactor. At 24% of the total height of the catalyst bed downstream of the hot spot which was located at 15% of the total height of the bed, 1 ppm of P, based on the weight of ethylene glycol used, in the form of triethyl phosphate was added to the synthesis gas. The reactor temperature was set to 365° C. by means of a salt melt.

The total amount of gas, consisting of circulated gas and synthesis gas, was 9150 standard l/h. The GHSV (gas hourly space velocity), which is defined as GHSV=Gas volume / catalyst volume, was 1610 h$^{-1}$. The LHSV (liquid hourly space velocity), which is defined as LHSV=Liquid volume / catalyst volume, was 0.13 h$^{-1}$. The residence time, defined as the quotient of the catalyst volume and the amount of gas, was 2.3 s.

After leaving the reactor, the reaction gas was contacted with water and the reaction products were dissolved in the aqueous phase. The permanent gases CO and CO$_2$ formed in the reaction remained in the off-gas and were analyzed in the gas phase.

After a running time of 10 days, a glyoxal yield of 74.4 mol %, based on ethylene glycol used, was achieved at an ethylene glycol conversion of 96.8 mol %. Combustion to give CO and CO$_2$ was 13 mol %. Further by-products formed were 1.6 mol % of glycol aldehyde and 4.8 mol % of formaldehyde.

EXAMPLE 4

7.2 kg of shaped copper bodies were installed in a tube reactor of stainless steel having an internal diameter of 55 mm to give a catalyst bed height of 250 cm (catalyst volume: 5.7 l). A synthesis gas mixture comprising 840 g of ethylene glycol, 1800 standard l of air and 150 standard l of nitrogen was passed per hour through the tube reactor. At 24% of the total height of the catalyst bed downstream of the hot spot which was located at 15% of the total height of the bed, 1 ppm of P, based on the weight of ethylene glycol used, in the form of triethyl phosphate was added to the synthesis gas. The reactor temperature was set to 365° C. by means of a salt melt.

The total amount of gas, consisting of circulated gas and synthesis gas, was 9150 standard l/h. The GHSV (gas hourly space velocity), which is defined as GHSV=Gas volume / catalyst volume, was 1610 h$^{-1}$. The LHSV (liquid hourly space velocity), which is defined as LHSV=Liquid volume / catalyst volume, was 0.13 h$^{-1}$. The residence time, defined as the quotient of the catalyst volume and the amount of gas, was 2.3 s.

After leaving the reactor, the reaction gas was contacted with water and the reaction products were dissolved in the aqueous phase. The permanent gases CO and CO$_2$ formed in the reaction remained in the off-gas and were analyzed in the gas phase.

After a running time of 10 days, a glyoxal yield of 75.8 mol %, based on ethylene glycol used, was achieved at an ethylene glycol conversion of 99.1 mol %. Combustion to give CO and CO$_2$ was 15.3 mol %. Further by-products formed were 0.8 mol % of glycol aldehyde and 4.7 mol % of formaldehyde.

We claim:

1. A process for preparing carbonyl compounds of the formula

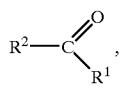

I where R$^1$ is a hydrogen atom or an alkyl radical having from 1 to 3 carbon atoms, R$^2$ is a hydrogen atom or a radical of the formula

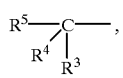

II where R$^3$ is a hydrogen atom or together with R$^4$ is an oxygen atom, R$^4$ is the radical OR$^6$ or together with R$^3$ is an oxygen atom, R$^5$ is a hydrogen atom, an alkyl radical having from 1 to 8 carbon atoms or a cyclohexyl or cyclopentyl radical and R$^6$ is an alkyl radical having from 1 to 4 carbon atoms, a cyclohexyl or cyclopentyl radical or a radical of the formula —CH$_2$—CHO or —CH$_2$—CH$_2$—O—CH$_2$—CHO, by gas-phase oxidation of methanol or alcohols of the formula

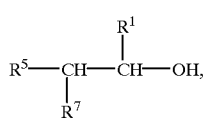

III where R$^1$ and R$^5$ are as defined above and R$^7$ is a hydrogen atom or a radical OR$^8$ and R$^8$ is a hydrogen atom, an alkyl radical having from 1 to 4 carbon atoms, a cyclohexyl or cyclopentyl radical or a radical of the formula —CH$_2$—CH$_2$—OH or —CH$_2$—CH$_2$—O—CH$_2$—CH$_2$—OH, using an oxygen-containing gas in the presence of copper- and/or silver-containing catalysts and an amount of a phosphorus compound which is volatile under the reaction conditions which is such that the amount of phosphorus (calculated as P) is up to 20 ppm, based on the weight of alcohol used, wherein the phosphorus is introduced within the catalyst bed.

2. A process as claimed in claim 1, wherein the phosphorus is introduced into the catalyst bed in the region of the upper 0.1–50% of the total height of the catalyst bed.

3. A process as claimed in claim 1, wherein the phosphorus is introduced in the region of the upper 1–35% of the total height of the catalyst bed.

4. A process as claimed in claim 1, wherein the amount of phosphorus (calculated as P) is from 0.05 to 20 ppm, based on the weight of the alcohol used.

5. A process as claimed in claim 1, wherein the phosphorus is introduced in at least two portions.

6. A process as claimed in claim 5, wherein the weight ratio of the first portion of phosphorus to the further portion or portions is from 0.005 to 200.

7. A process as claimed in claim 1, wherein glyoxal is prepared from ethylene glycol.

* * * * *